United States Patent [19]

Alkan et al.

[11] Patent Number: 4,919,973
[45] Date of Patent: Apr. 24, 1990

[54] COATING APPARATUS FOR SMALL-SCALE PROCESSING

[75] Inventors: M. Hayat Alkan, Chicago; Michael J. Groves, Lincolnshire, both of Ill.

[73] Assignee: Board of Trustees of the University of Illinois, Chicago, Ill.

[21] Appl. No.: 109,229

[22] Filed: Oct. 16, 1987

[51] Int. Cl.⁵ .............................................. B05D 1/22
[52] U.S. Cl. .................................... 427/213; 118/303; 118/DIG. 5
[58] Field of Search .................. 427/213; 118/DIG. 5, 118/305

[56] References Cited

U.S. PATENT DOCUMENTS 2,667,706  2/1954  Morse et al. .................. 118/DIG. 5
4,656,056  4/1987  Leuenberger ......................... 427/213
4,685,419  8/1987  Nakajima .................. 118/DIG. 5 X

FOREIGN PATENT DOCUMENTS 45-37123  11/1970  Japan .................................... 427/213

OTHER PUBLICATIONS

Seitz, J. A., et al.: Ch. 12: Tablet Coating in *The Theory and Practice of Industrial Pharmacy*, 3rd Ed., Edited by L. Lachman, et al., Lea and Febiger, Philadelphia, pp. 346–373, (1986).

*Primary Examiner*—Shrive Beck
*Attorney, Agent, or Firm*—Marshall, O'Toole, Gerstein, Murray & Bicknell

[57] ABSTRACT

The present invention provides methods and materials for coating relatively small quantities of particles including tablets, pellets or granules. The device effectively fluidizes the particles to be coated by controlled vibration of a perforated platform through which drying air is passed during intermittent spraying of the particles with a solution of organic or aqueous-based coating material. The method coats individual tablets having as low a mass as 50 mg and coats quantities ranging from less than about 50 mg to 10 g of tablets, pellets, or granules.

3 Claims, 5 Drawing Sheets

COATING APPARATUS FOR SMALL-SCALE PROCESSING

BACKGROUND OF THE INVENTION

The present invention relates generally to systems for coating relatively small quantities of variously shaped materials and more particularly to systems for preparing coated tablets, pellets, or granules in quantities of from less than about 50 mg to 10 g. In a preferred embodiment, the present invention provides devices which effectively fluidize particulate materials to be spray coated by controlled vibration of a perforated bed through which drying air is passed. The methods and apparatus provided by the present invention allow for small-scale production of coated tablets, pellets or granules and are especially useful in dealing with small quantities of scarce or expensive materials, e.g., drugs during the initial stages of formulation and development.

The preparation of coated tablets, pellets and granules is a common pharmaceutical process used to mask the taste of a drug, to improve drug appearance and stability, and/or to control drug release. See, e.g., Seitz, J. A., et al.,: Ch. 12: Tablet Coating in *The Theory and Practice of Industrial Pharmacy*, 3rd Ed. Edited by L. Lachman, et al., Lea and Febiger, Philadelphia, 1986. The coatings are commonly applied by spraying solutions of coating material into rotating drums containing the solid dosage form of the drug or by spraying coating solutions into fluidized or spouting beds, such as Wurster columns. Fluidization of the materials to be coated is ordinarily achieved in a columnar chamber by the upward flow of drying air. While these methods are generally effective for large-scale production, they are not readily applied in small scale contexts where the drug to be coated is either not readily available in large quantities or is relatively expensive. The smallest rotating drum method currently available is believed to require use of at least 10–100 g of material to be coated and the smallest fluid bed devices currently available are believed to require a minimum of about 0.5 kg of material.

In sum, no prior devices or methods have been totally responsive to the need in the art for devices and methods allowing for the coating of small particles in quantities of ten grams or less.

BRIEF SUMMARY OF THE INVENTION

The present invention provides improved methods for the uniform application of one or more layers of coating materials to variously shaped particles, which methods are quite advantageously applied to small (50 mg to 10 g) quantities of particles. According to these improved methods, particles to be coated are fluidized by application of vibratory energy of selected amplitude and frequency in the course of spray coating and drying.

Apparatus of the present invention is seen to generally comprise a container for particles to be coated having a particle support means at its base and further having a means for providing vibratory energy to the support. The apparatus also includes means for supplying gas (preferably air) flow to the particles as well as means (preferably in the form of an airbrush sprayer) for applying fluid coating materials to the particles. In operation, particles are disposed on the support and caused to vibrate and become fluidized during application of the coating material and application of a drying gas flow to the particles. Intermittent application of coating materials during essentially continuous application of vibratory energy and/or gas flow results in development of uniform multilamellar coating of particles.

In preferred configurations, the support provided af the base of the container has upper and lower sides (the particles being supported on the upper side) and is perforated. Gas flow is supplied to the lower side of the support and through the perforations. In an alternative conformation, gas flow may be provided by providing a decreased pressure beneath the perforated support, drawing, e.g., air down through the perforations.

Granules coated according to the invention with aqueous or organic solutions of acrylic resins, such as Eudragits ™ RL100, L100-55, and L30D, are attractive in appearance; the release of an incorporated drug, such as quinacrine dihydrochloride, is delayed as a direct function of the coating load. The coating process is rapid, quantitative and economical and may be used with organic solvent or aqueous based systems. The invention advantageously allows for gravimetric measurement of the amount of coating applied. The method of small-scale coating is especially useful when dealing with small quantities of expensive drugs at the initial stages of formulation and development.

Other aspects and advantages of systems of the present invention will be apparent upon consideration of the following detailed description thereof which includes numerous illustrative examples of the practice of the invention, reference being made to the drawing wherein.

DETAILED DESCRIPTION

The following examples illustrate practice of the invention by which the small-scale coating of particles, including tablets, pellets, or granules, in quantities of from less than about 50 mg to 10 g, is achieved. More specifically, Example 1 illustrates the assembly of the coating apparatus; Example 2 illustrates the preparation of model compound granules to be coated; Example 3 relates to exemplary coating procedures employing the apparatus of Example 1; and, Example 4 describes the dissolution testing of products.

The examples which follow are for illustrative purposes are not intended in any way to limit the scope of the invention.

EXAMPLE 1

Figure 1:
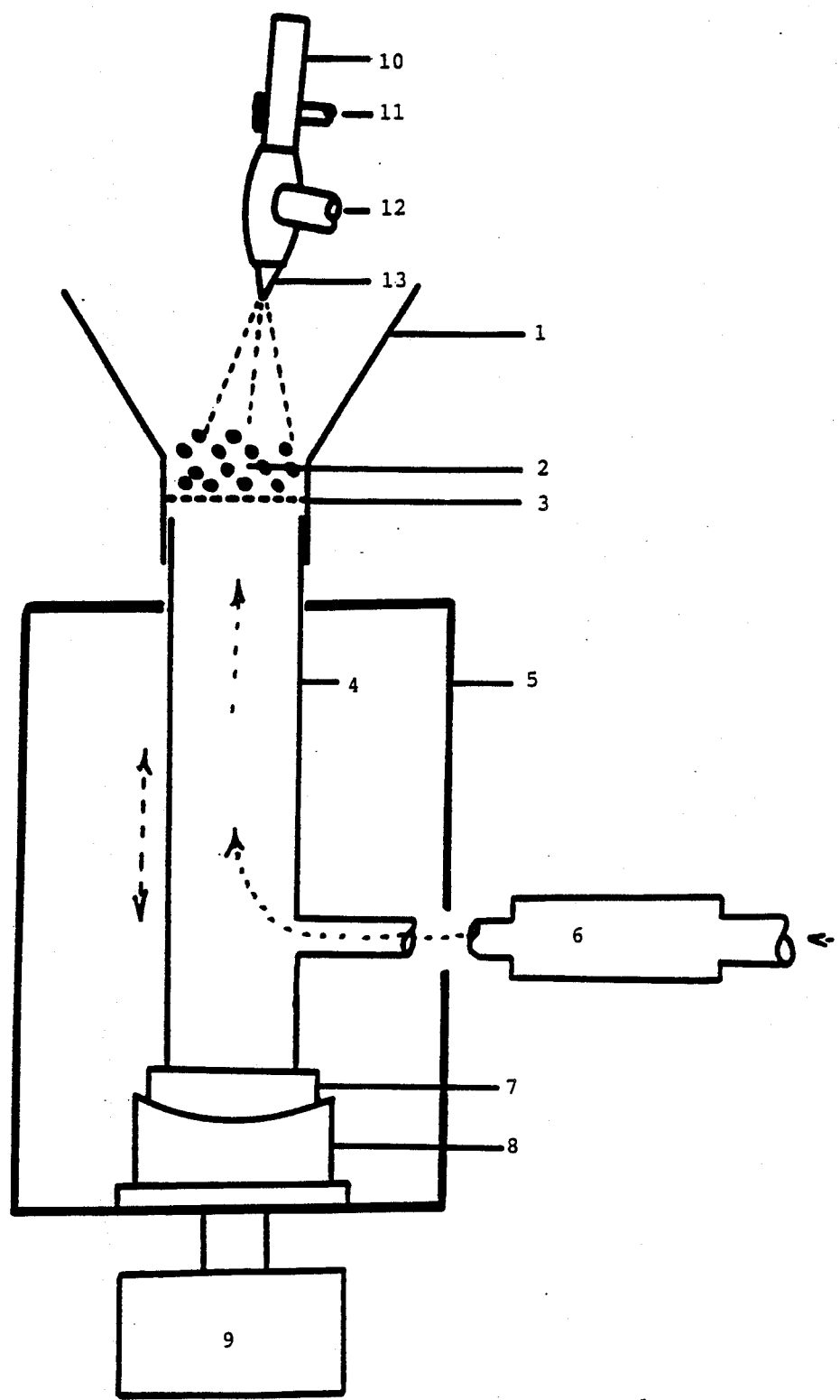
FIG. 1 is a sectional view of apparatus of the invention.

FIG. 1 depicts a schematic diagram of a small-scale coating device: (1) polyethylene funnel; (2) fluidized particulate; (3) 35 mesh sieve inserted into funnel; (4) supporting tube; (5) supporting framework; (6) air inlet and 'Drierite' tube; (7) metal lid glued onto amplifier loud speaker diaphragm; (8) amplifier, having a loud speaker output; (9) driver amplifier; (10) airbrush; (11) air inlet; (12) coating solution; (13) binary nozzle.

In a preferred embodiment, the conical funnel (1) is made of polyethylene and has an upper internal diameter of 100 mm and a lower internal diameter of 40 mm. The funnel is cut at the apex of the core, and a 35 mesh polyethylene sieve (3) inserted between the upper and lower portions and glued into position (polyisothiocyanate cement, Krazy Glue Inc., Itasca, Ill.).

The funnel (1) is supported on a parallel sided polyethylene tube (4), 40 mm external diameter to provide a close fit. The tube (4) has a side piece connected, through a silicon rubber tube and a cylinder (6) of indicating "Drierite" silica gel, to a tank of compressed gas (e.g., air). At the lower end, the tube (4) is glued to a metal screw capped lid (7), 70 mm diameter, itself glued to an elastomeric membrane, such as that of a loudspeaker (8). In both cases, the adhesive used is a silicon rubber cement (Dow, Midland, Mich.).

In this embodiment, the loudspeaker (8) is a 10 cm Realistic (Radio Shack) woofer speaker (model number 40-1022), 5W nominal power over a range of 55–5000 Hz. Amplitude adjustment is achieved with a Realistic Model SA-15 Integrated Stereo Amplifier (9). Frequency is controlled with a Dynascan Corp B and K Precision Solid State Model E-310B sine/square wave generator, forming a part of amplifier (9).

Calibration of both amplitude and frequency is obtained by vertically moving a paper chart at a predetermined speed past a pen attached to the upper part of the funnel (1).

Coating solutions are applied to the upper side of the vibrating bed by means of a 'Paasche' brand artists' airbrush (10), using jets as appropriate, and driven by a compressed air tank.

EXAMPLE 2

Granules are prepared from quinacrine dihydrochloride (Aldrich Chemical Co.) and lactose or soy protein (food grade soy protein isolate-"ARDEX R" brand, Archer, Daniel Midland) by wet granulation using a 60% aqueous sucrose syrup or water, forced through a 3.36 mm stainless steel mesh and dried at 25°±1° C. overnight. Dried granules are separated into fractions using a 3" vibratory sieve shaker (Gilson, Model SS-5) through sieves with apertures varying from 0.075 to 2.83 mm. Granules prepared using PVP (Polyvinyl Pyrrolidone, GAF Corporation) as a binder are too fragile to be vibrated during the coating process. Testing is carried out on two basic granule formulations consisting of either:

|    |                            |        |
|----|----------------------------|--------|
|    | quinacrine dihydrochloride | 19.2 g |
|    | lactose                    | 72.0 g |
|    | sucrose (as syrup) dry weight | 8.9 g |
| or |                            |        |
|    | quinacrine dihydrochloride | 20.0 g |
|    | soy protein                | 80.0 g |
|    | water                      | 9.5 g  |

EXAMPLE 3

Depending on the quantity and size of the material to be coated, the amplitude and frequency of the vibration of the mesh and the velocity of the dry air is empirically adjusted to allow the bed to oscillate without material spilling over the sides of the funnel. As used herein, this empirically adjusted amplitude and frequency is referred to as the effective amplitude and frequency. The exemplary coating solutions used included:

Eudragit RL100, 6 to 9% w/v in chloroform;
Eudragit L30D in 20% aqueous propylene glycol; and
Eudragit L100-55 30% w/v dissolved in aqueous 1N sodium hydroxide.

Coating solution was manually applied by positioning the nozzle of the airbrush a suitable distance (e.g., 5–7 cm) from the surface of the bed and using short, three to five second bursts at 2 minute intervals to allow each consecutive coat to dry. Coating is carried out at ambient room temperature (approximately 25° C.). A typical set of conditions for a 1 g load of lactose granules, mean diameter 1.85 mm, sprayed with a solution of Eudragit RL100 6% in chloroform is as follows:

| amplitude        | 3.25 mm   |
|------------------|-----------|
| frequency        | 23 Hz     |
| dry air pressure | 12 psig   |
| spray            | 5 psig    |
| spray nozzle     | 1.5 turns |

Coating is continued until a required mass/unit area of coating has been built up on the granules or until the requisite amount of coating has been applied as determined from the weight increase of the granules. All coating procedures are carried out in a chemical fume hood. A thin coating of Eudragit RL100 is first applied before application of the aqueous soluble coatings in order to avoid dissolving the water soluble granule constituents, for example lactose.

EXAMPLE 4

Dissolution testing was carried out according to the USP XXI, Apparatus 2, method with the paddles rotating at 50 rpm in 1L distilled water or phosphate buffer at 37° C. as the dissolution medium. The apparatus is a six station Vanderkamp ® model 600 USP dissolution tester with a VanKel Model 2500 external circulator and an auto sampling peristaltic driving pump, all by VanKel Industries Inc. Absorbance at 425 nm is continuously determined throughout the dissolution run by means of a Perkin-Elmer Lambda 3B uv/vis spectrophotometer fitted with a Model 3600 data station and Model 660 printer. Dissolution rates for comparative studies are estimated and are defined as the time required for 50% or 15% ($t_{50}$, $t_{15}$) of the drug to be released.

Initial experiments using beeswax containing methylene blue as a coating indicated that this type of coat was less even and regular than desired and examination under a low power microscope revealed some folds, cracks and cavities in the coatings. However, coatings with the 'Eudragit' resins are visually glossy and uniform in appearance under the microscope. Generally, batches of particles weighing from approximately 0.1 g to 10 g can be successfully coated according to the device and method of the invention. Individual particles ranging in size from approximately 100 microns to approximately several mm in length have been successfully coated; in addition individual tablets weighing as little as 100 mg may also successfully be coated, as may small, 50 mg, compacted pellets.

Figure 2:
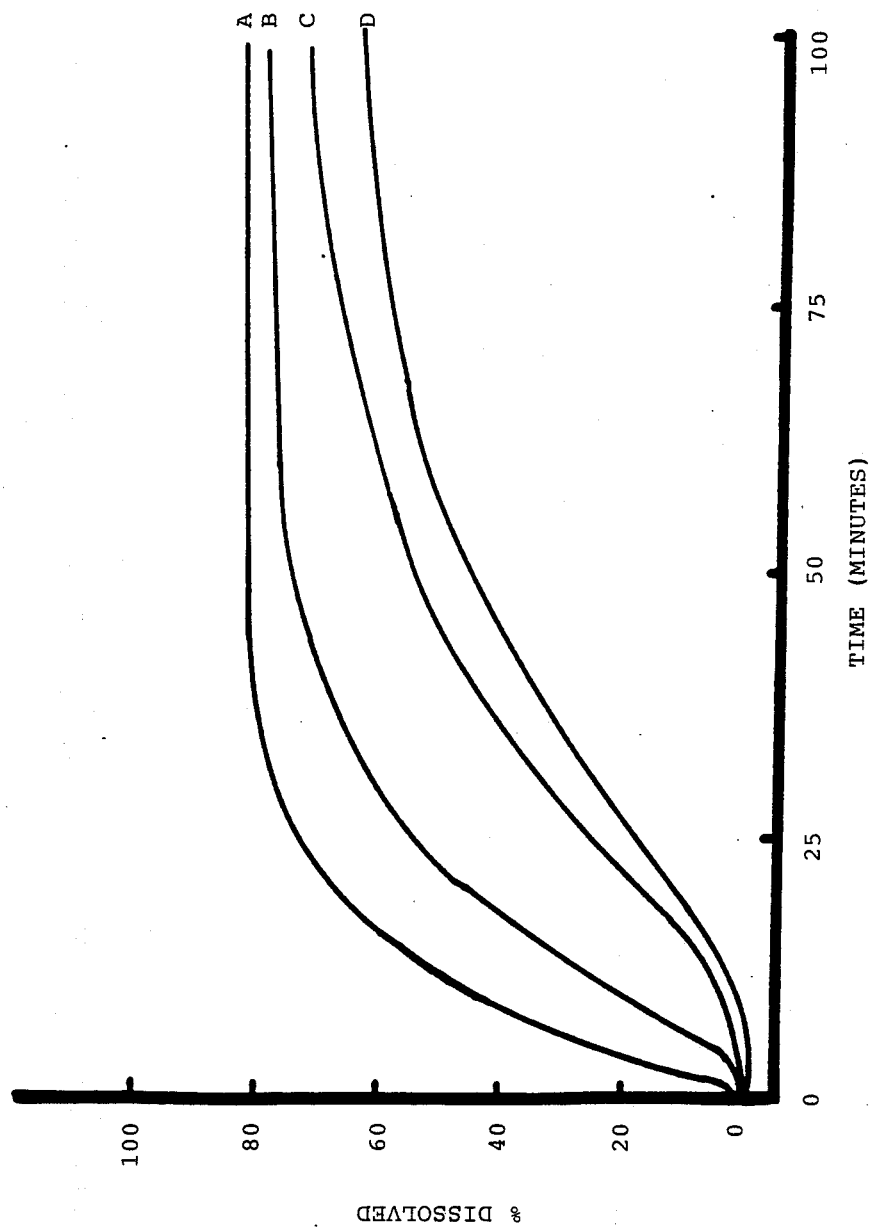
FIGS. 2 and 3 are graphic representations of dissolution profiles of granules coated according to the invention.
Figure 3:
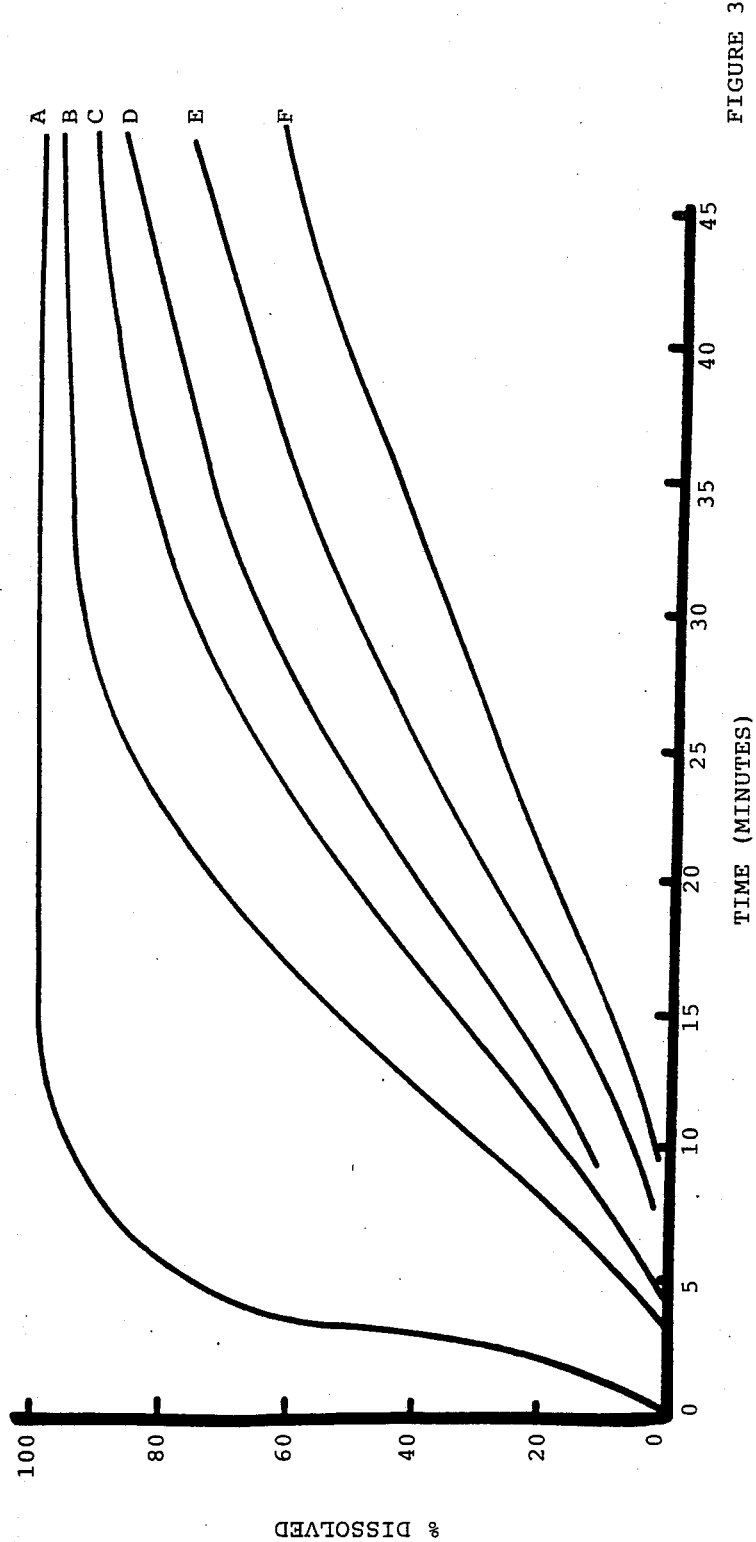

FIG. 2 depicts the dissolution profiles obtained for granules containing quinacrine dihydrochloride coated with different loading of Eudragit RL. The granules made from lactose and sucrose were coated as follows: A. uncoated; B. 3 mg/cm$^2$; C. 6 mg/cm$^2$; and D. 7 mg/cm$^2$. FIG. 3 also depicts dissolution profiles obtained for granules containing quinacrine dihydrochloride coated with different loading of Eudragit RL, however, these granules were made from soy protein and were coated as follows: A. uncoated; B. 1.3 mg/cm$^2$; C. 2.3 mg/cm$^2$; D. 3.3 mg/cm$^2$; E. 4.4 mg/cm$^2$; and F. 6.2 mg/cm$^2$.

Figure 4:
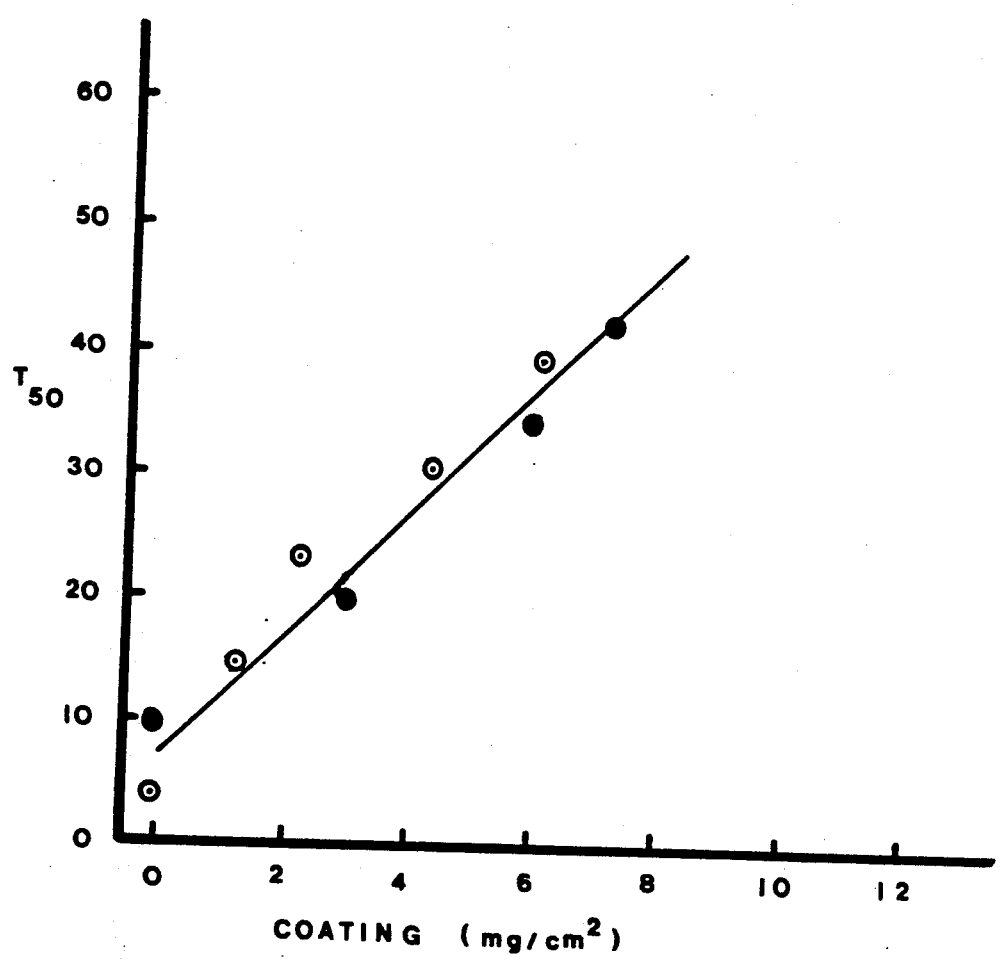
FIG. 4 is a graphic comparison of release rates from different formulations of granules coated with differing thicknesses of coating according to the invention.
Figure 5:
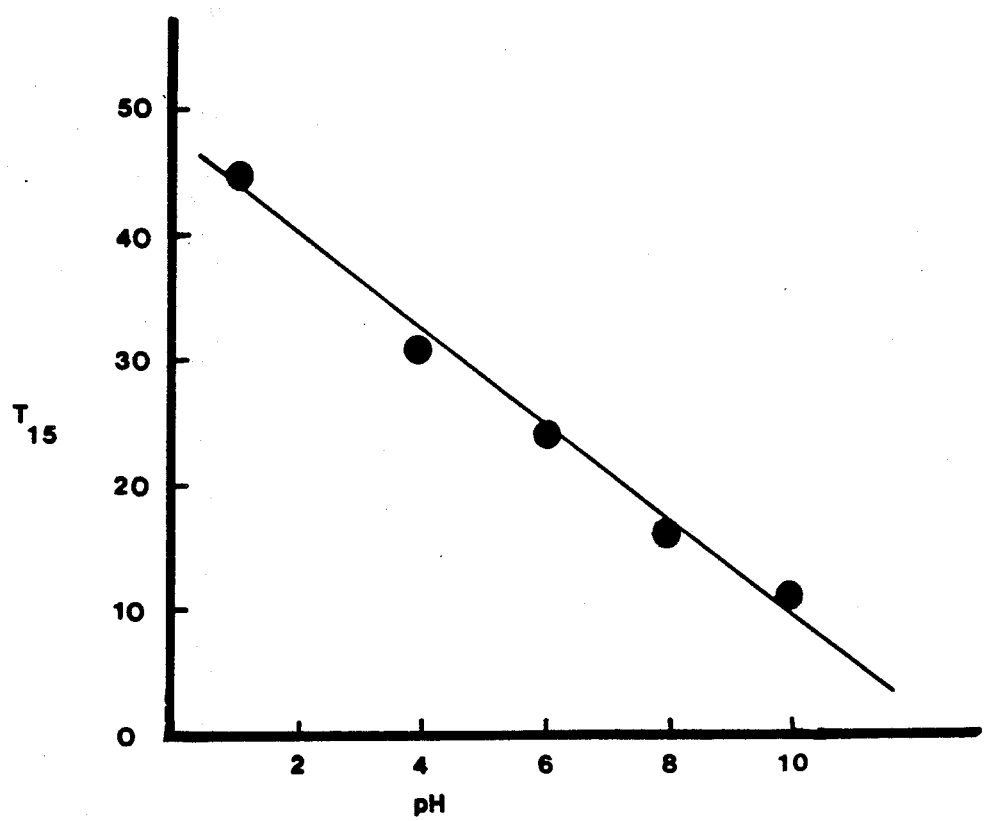
FIG. 5 is a graphic representation of the effect of pH on granules coated with an enteric coating according to the invention.

FIG. 4 shows a comparison of the release rates from different formulations of granules containing quinacrine dihydrochloride as a function of Eudragit RL coating and incorporates data from FIGS. 2 and 3: open-circles: lactose/sucrose ($r^2=0.992$); and closed-circles: soy protein ($r^2=0.992$). FIG. 5 shows the effect of pH on the initial ($t_{15}$) release of quinacrine dihydrochloride from lactose/sucrose granules coated with 7.9 mg/cm$^2$ Eudragit L30D (mean of duplicate tests) ($r^2=-0.995$).

By increasing the coating load, the dissolution rate of the coated materials is slowed appreciably and predictably as illustrated in FIGS. 2-4. In addition, FIG. 5 illustrates the dissolution rate of granules coated with a pH sensitive material. The release rate of the drug from soluble or insoluble granules coated with a permeable but insoluble film (Eudragit RL) decreases directly with an increase in the amount of coating applied and the release process is unaffected by the granule formulation (FIG. 4). The dissolution experiments for enteric coated granules clearly indicate that the rate of release of the drug is a function of the solubility of the coating material (FIG. 5). The dissolution rate as a function of pH is measured only at the initial stages of dissolution, i.e., at 15 minutes, because at later stages, the dissolution process is additionally affected by the decrease in solubility of the drug itself. The drug used in this study is a base and its solubility should be lower at higher pH. However, for the initial stages of dissolution the variable solubility of the drug as a function of pH should not affect the rate of dissolution as long as sink conditions persist. All of these results indicate that an even coat of constant thickness was achieved using the device and method of the invention.

It is noteworthy that if sufficient coats of 'Eudragit' are applied to a water soluble particulate material, upon exposure to aqueous conditions the core material dissolves and permeates through the insoluble but permeable coat. Thin hollow shells of the coating are left having the shape of the soluble granule or pellet originally forming the matrix. These shells are completely formed and have no gaps, demonstrating the uniformity with which the coating is applied using the systems of the invention.

As is also true for other fluidization processes, the physical formulation of the particles or granules is quite significant since they must be hard enough to resist abrasion during the tumbling and collisions involved during the vibration phase of the method.

The foregoing illustrative examples relate to a small-scale coating apparatus for coating small amounts of variously shaped particles. While the present invention has been described in terms of a specific device and method, it is understood that variations and modifications will occur to those skilled in the art upon consideration of the present invention.

For example, it is envisioned that methods other than use of a loudspeaker membrane could be used to generate vibratory energy to fluidize the particles to be coated; for example a mechanical oscillatory cam and piezo electric devices may be equally effective. Also, while the application of a specific film coating has been described, it will be apparent that other coatings such as sugar coatings, syrup coatings, wax coatings, seal coatings, cellulosic and other polymeric coatings may be employed in practice of the invention. Moreover, plasticizers, colorants and similar additives may readily be incorporated in the coating material. Further, while the coating of drugs has been described, the coating of other small particles, such as precious jewels, pearls, diamonds, electronic components, and small mechanical components, such as ball-bearings and the like, with metal coatings, lubricants, anti-oxidants, gelatins, protective coatings and the like may readily be accomplished according to the invention.

Numerous modifications and variations in the invention as described in the above illustrative examples are expected to occur to those skilled in the art and consequently only such limitations as appear in the appended claim should be placed thereon.

Accordingly, it is intended in the appended claims to cover all such equivalent variations which come within the scope of the invention as claimed.

What is claimed is:

1. In a method for coating variously shaped particles and comprising the steps of:
    fluidizing said particles,
    spraying coating materials onto said particles to form coated particles, and
    subjecting said particles to gas flow to dry said coated particles,
    the improvement comprising:
    the step of fluidizing said particles solely through application of vibratory energy of varying amplitude and frequency, and
    the step of directing downwardly said gas flow to dry said coated particles.

2. An apparatus for coating variously shaped particles with coating materials, said apparatus comprising:
    container means for said particles, said container means having a base;
    support means at said container base, having upper and lower sides and capable of supporting said particles on said upper side;
    means for supplying vibratory energy of variable amplitude and frequency to said support means to fluidize said particles supported on said upper side;
    means for supplying said coating materials to uniformly coat said fluidized particles;
    means for supplying a flow of drying gas to dry said fluidized, coated particles;
    said support means having perforations through which said drying gas is flowed;
    and said means for supplying said flow of drying gas comprises means or drawing said gas downwardly through said perforations.

3. An apparatus as recited in claim 2 wherein:
    said means for supplying said vibratory energy comprises means capable of fluidizing said particles when said drying gas is drawn downwardly through said perforations.

* * * * *

UNITED STATES PATENT AND TRADEMARK OFFICE
CERTIFICATE OF CORRECTION

PATENT NO.   : 4,919,973
DATED        : April 24, 1990
INVENTOR(S)  : M. Hayat Alkan, et al.

It is certified that error appears in the above-identified patent and that said Letters Patent is hereby corrected as shown below:

Column 6, line 57, "or" should be --for--.

Signed and Sealed this

Twenty-second Day of December, 1992

Attest:

DOUGLAS B. COMER

*Attesting Officer*     Acting Commissioner of Patents and Trademarks